United States Patent
Schöning et al.

(10) Patent No.: US 7,019,161 B2
(45) Date of Patent: Mar. 28, 2006

(54) PROCESSES FOR THE PREPARATION OF 3-AMINOCARBOXYLIC ACIDS AND THEIR ESTERS

(75) Inventors: Kai-Uwe Schöning, Windisch (CH); Martin Studer, Basel (CH); Hans Jürg Kirner, Pratteln (CH); Stephan Burkhardt, Gelterkinden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 160 days.

(21) Appl. No.: 10/313,041

(22) Filed: Dec. 6, 2002

(65) Prior Publication Data

US 2003/0149270 A1 Aug. 7, 2003

(30) Foreign Application Priority Data

Dec. 7, 2001 (EP) .................................. 01811197

(51) Int. Cl.
C07C 261/00 (2006.01)
C07C 229/00 (2006.01)
C07C 205/00 (2006.01)

(52) U.S. Cl. ........................ 560/165; 562/433; 562/553
(58) Field of Classification Search ................ 560/155, 560/165; 562/433, 553
See application file for complete search history.

(56) References Cited

U.S. PATENT DOCUMENTS 4,585,887 A * 4/1986 Jolidon et al. ................ 560/38

FOREIGN PATENT DOCUMENTS

EP 0 144 980 6/1985

OTHER PUBLICATIONS

Cimarelli et al, (2001), Synthetic Communications, 31(19) pp. 2943-2953.*

Cimarelli et al, (1996) Journal of Organic Chemistry, 61(16), pp. 5557-5563.*
Furukawa et al, Chemical and Pharmaceutical Bulletin (1979) pp. 2223-2226.*
Bartoli et al, Journal of Organic Chemistry (1994) 59(18, pp. 5328-5335.*

* cited by examiner

Primary Examiner—J. Parsa
(74) Attorney, Agent, or Firm—Kevin T. Mansfield

(57) ABSTRACT

The present invention relates to novel processes for the preparation of optically active 3-aminocarboxylic acids and their esters, in particular processes for the preparation of optically active compounds of the formula IA or IB

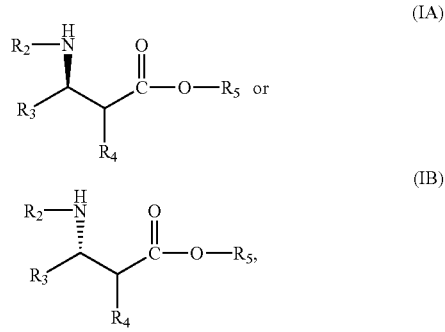

as free bases or as acid addition salts thereof, in which the radicals are as defined in the description; in particular using the catalytic hydrogenation of olefinic precursors in the presence of platinum on alumina as a catalyst and the removal of chiral auxiliary groups from salt precursors; and novel process sections in the route for their synthesis, and processes for the preparation of biologically, in particular pharmacologically, active compounds, which comprise the novel processes.

7 Claims, No Drawings

PROCESSES FOR THE PREPARATION OF 3-AMINOCARBOXYLIC ACIDS AND THEIR ESTERS

SUMMARY OF THE INVENTION

The present invention relates to novel processes for the preparation of optically active 3-aminocarboxylic acids and their esters, and novel process sections in the route for their synthesis, and processes for the preparation of biologically, in particular pharmacologically, active compounds, which comprise the novel processes.

BACKGROUND OF THE INVENTION

3-Aminocarboxylic acids (β-amino acids) are important products which are contained in naturally occurring peptides and are important chiral structural units for the synthesis of β-lactam antibiotics, and also for other pharmaceutically active substances, e.g. anti-platelet agents (see, for example, Zablocki et al., J Med. Chem. 36, 1811 (1993), Bovy et al., Bioorg. Med. Chem. 2, 881–895 (1994), Zablocki et al., J. Med. Chem.,38, 2378, U.S. Pat. No. 5,424,334 and U.S. Pat. No. 5,481,021), immunomodulating compounds (see, for example, Suda et al., J. Antibiotics 29, 100 (1976)), hypotensive agents (see, for example, Chaturvedi et al., J. Med. Chem. 13, 177 (1970), Lizuk et al., J. Chem. Soc. Chem. Commun. 1989, 1978, and Okino et al., Tetrahedron Lett. 34, 501 (1993)), or anticancer agents (see, for example, Denis et al., J. Org. Chem. 55, 1957 (1990)).

The object of the present invention is the provision of a process which makes possible the preparation of optically active 3-aminocarboxylic acid derivatives in a particularly advantageous manner, in particular in high optical purity and/or high yields.

GENERAL AND DETAILED DESCRIPTION OF THE INVENTION

The present invention relates to a process for the preparation of optically active compounds of the formula IA or IB

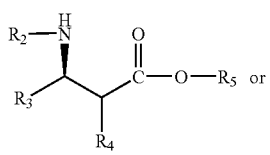
(IA)

or

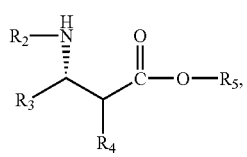
(IB)

as free bases or as acid addition salts thereof, in which $R_2$ is hydrogen, unsubstituted or substituted alkyl, or unsubstituted or substituted aryl, $R_3$ is—in each case unsubstituted or substituted—alkyl, aryl or heterocyclyl, or esterified carboxyl, $R_4$ is hydrogen (preferred), unsubstituted or substituted alkyl, mono- or disubstituted amino, hydroxyl, unsubstituted or substituted alkoxy or unsubstituted or substituted aryloxy, or $R_3$ and $R_4$, together with the carbon atoms connecting them, form a 5- or 6-membered ring, and $R_5$ is hydrogen, unsubstituted or substituted alkyl, unsubstituted or substituted aryl or organic silyl, wherein a compound of the formula II

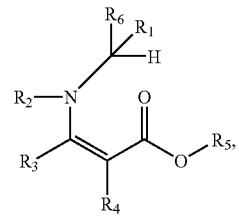
(II)

in which $R_1$ and $R_6$ are—in each case unsubstituted or substituted—alkyl, aryl or heterocyclyl, with the proviso that $R_1$ is a radical other than $R_6$ and that at least one of the two radicals is unsubstituted or substituted aryl or unsubstituted or substituted heterocyclyl, in particular aryl, and $R_2$, $R_3$, $R_4$ and $R_5$ are as defined for compounds of the formula IA or IB, is hydrogenated in the presence of a catalytically active amount of a heterogeneous hydrogenation catalyst with saturation of the double bond to give compounds of the formulae IIA and/or IIB,

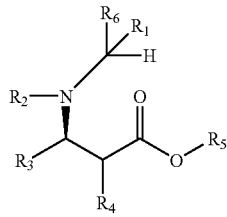
(IIA)

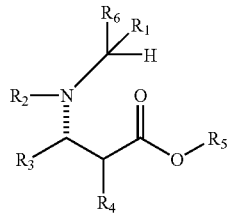
(IIB)

in which the radicals $R_1$ and $R_6$ are as defined for compounds of the formula II and the radicals $R_2$, $R_3$, $R_4$ and $R_5$ are as defined for compounds of the formulae IA and IB;

then this product obtained is converted using an acid of the formula $[H^+]_n X^{n-}$, in which n is 1 to 3 and X is an acid radical, into a corresponding acid addition salt of the formulae IIIA and/or IIIB respectively,

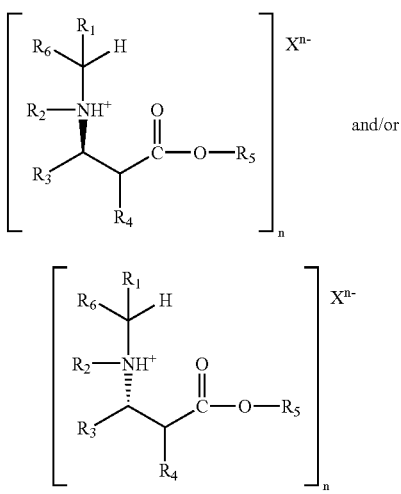

in which n is an integer greater than or equal to 1, in particular 1 to 3, the radicals $R_1$ to $R_6$ are as defined for compounds of the formula II and $X^{n-}$ is an acid anion, and the salt obtained is crystallized;
then the chiral auxiliary group $R_1R_6CH$— is removed, and thus a salt of the formula IVA or IVB is obtained,

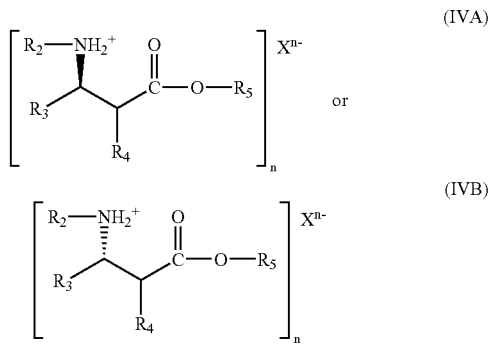

in which n and the radicals $R_2$ to $R_5$ are as defined for compounds of the formula IA or IB and $X^{n-}$ is an acid anion, and, if desired, an acid addition salt of the formula IVA or IVB obtained is converted in the presence of a base into the free compounds of the formula IA or IB; and/or, if desired, the group $R_5$ is removed from an ester of the formula IVA or IVB if it has another of the meanings mentioned apart from hydrogen.

A general embodiment of the invention also relates to a process which comprises the removal of the chiral auxiliary group from an acid addition salt of the formula IIIA or IIIB to give a salt of the formula IVA or IVB and, if desired, the conversion into the free compounds of the formula IA or IB subsequently in the presence of a base.

It has surprisingly been found that the choice of the sequence of the removal of the chiral auxiliary group from acid addition salts of the formula IIIA or IIIB to give salts of the formula IVA or IVB and the subsequent conversion into the free bases of the formula IA or IB brings about an unexpected increase in yield compared with the reverse sequence (firstly conversion into the free base, then removal of the chiral auxiliary group). In particular, by means of the removal of the chiral auxiliary group from the acid addition salt instead of the free base, a lower amount of heterogeneous catalyst (such as Pd/C) can be used. If only the salts of the formula IVA or IVB are to be obtained, the conversion into the free base can be omitted (the acid addition salts of the formulae IVA and IVB in each case correspond to salts of compounds of the formula IA or IB).

A preferred aspect of the invention also relates to a process for the preparation of compounds of the formula IIA and/or IIB by hydrogenation of a compound of the formula II in the presence of platinum on alumina as a catalyst—this reaction proceeds with a very much lower amount of noble metal than previously used reactions and makes possible high yields and diastereomeric excesses of the compounds of the formula IIA and/or IIB obtained.

Further advantages of the processes according to the invention are evident from the details and preferred embodiments mentioned below.

The invention also relates to processes for the preparation of derivatives of the compounds of the formula IA or IB having biological, in particular pharmacological, action, which comprise the preparation processes mentioned above and below for compounds of the formula IA or IB.

The general terms used above and below (including the reactions and reaction conditions) preferably are as defined below, if not stated otherwise—these specific definitions and reaction descriptions can be used independently of one another instead of the general terms mentioned above and below, which in each case leads to preferred embodiments of the invention:

Substituted in particular means that the radicals mentioned in each case are substituted by one or more, in particular one to three, radicals selected independently of one another from aryl, in particular phenyl or naphthyl (where aryl, in particular phenyl or naphthyl, is substituted by one or more, in particular up to three, substituents, preferably selected independently of one another from alkyl, in particular lower alkyl, especially ethyl or primarily methyl, hydroxyl, etherified hydroxyl, preferably alkoxy, in particular lower alkoxy, especially ethoxy or in particular methoxy, or phenyl-lower alkoxy, mono- or disubstituted amino, in particular N-alkylamino, in particular N-lower alkylamino, or N,N-dialkylamino, in particular N,N-di-lower alkylamino, and halogen, or in a broader embodiment of the invention additionally selected from halo-lower alkyl, in particular trifluoromethyl, cyano, nitro, sulfamoyl, esterified carboxyl, such as lower alkoxycarbonyl or phenyl-lower alkoxycarbonyl, and lower alkanoyloxy); heterocyclyl, in particular such as defined below; from hydroxyl; from esterified carboxyl, such as lower alkoxycarbonyl or phenyl-lower alkoxycarbonyl; from etherified hydroxyl, preferably alkoxy, in particular lower alkoxy, or phenyl-lower alkoxy; from unsubstituted, mono- or disubstituted amino, preferably N-alkylamino, in particular N-lower alkylamino, or N,N-dialkylamino, in particular N,N-di-lower alkylamino; and from halogen, furthermore from thio and substituted thio.

Etherified hydroxyl is in particular unsubstituted or substituted alkyloxy, unsubstituted or substituted aryloxy or aryl-lower alkyloxy, preferably lower alkoxy or phenyl-lower alkoxy.

Substituted thio is in particular unsubstituted or substituted alkylthio, unsubstituted or substituted arylthio or aryl-lower alkylthio, preferably lower alkylthio or phenyl-lower alkylthio.

Esterified carboxyl is in particular (unsubstituted or substituted alkyl)-oxycarbonyl or aryloxycarbonyl, in particular lower alkoxycarbonyl or phenyl-lower alkoxycarbonyl.

Mono- or disubstituted amino is preferably N-mono- or N,N-di-(unsubstituted or substituted alkyl)-amino, N-(unsubstituted or substituted aryl)amino, N-(unsubstituted or substituted alkyl)-N-arylamino or N,N-diarylamino, or lower alkanoylamino, in particular N-mono- or N,N-di-lower alkylamino.

In N-substituted amido, the amide nitrogen is preferably substituted as defined above for mono- or disubstituted amino, in particular N-mono- or N,N-di-lower alkyl- or -phenyl-lower alkylamino.

It is clear to the person skilled in the art that substituents of this type can only be present in positions in which they are chemically possible and, for example, if double bonds are present, lead to stable chemical compounds, it being possible for the person skilled in the art to decide on the basis of his/her expert knowledge or of simple routine experiments which compounds fulfil these criteria.

The prefix "lower" or "Lower" means that the corresponding radical preferably has up to 7 carbon atoms, in particular up to 4 carbon atoms. Lower alkyl is thus preferably $C_1$–$C_7$alkyl, in particular $C_1$–$C_4$alkyl, and can be unbranched or branched once or more than once, if possible. Unsaturated radicals, such as lower alkenyl or lower alkynyl, have at least 2 to 7, in particular 3 to 7, especially 3 to 4 carbon atoms.

Unsubstituted or substituted alkyl is in particular $C_1$–$C_{10}$alkyl which is linear or branched once or more than once, in particular lower alkyl, where in the case of substitution, as substituents, one or more, preferably up to to three, substituents selected independently of one another from those mentioned above under "substituted" are preferred.

Unsubstituted or substituted aryl is in particular $C_6$–$C_{14}$aryl, where aryl can mean an individual ring or a radical composed of two or three fused rings, in particular phenyl or naphthyl, where in the case of substitution, as substituents, one or more, preferably up to three, substituents selected independently of one another from those mentioned above under "substituted" are preferred.

Heterocyclyl is preferably a heterocyclic radical which is saturated or furthermore wholly or partially unsaturated (double bonds preferably being present in conjugated form, in particular in aromatic systems (heterocyclyl is then described as heteroaryl)), and is preferably a mono-, bi- or tricyclic ring system; preferably has 3 to 24, in particular 4 to 16, ring atoms; where one or more, in particular one to three, ring atoms are heteroatoms, in particular selected from nitrogen, oxygen or sulfur, and where heterocyclyl is unsubstituted or, in particular, substituted as described under "substituted". Examples of heterocycles of this type are imidazolyl, thienyl, furyl, tetrahydrofuryl, pyranyl, thiopyranyl, thianthrenyl, benzofuranyl, chromenyl, pyrrolyl, pyrrolidinyl, imidazolyl, imidazolidinyl, benzimidazolyl, pyrazolyl, pyrazinyl, pyrazolidinyl, pyranyl, thiazolyl, isothiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, indolyl, benzimidazolyl, coumaryl, indazolyl, triazolyl, purinyl, 4H-quinolizinyl, isoquinolyl, quinolyl, tetrahydroquinolyl, tetrahydroisoquinolyl, decahydroquinolyl, benzofuranyl, dibenzofuranyl, benzothiophenyl, dibenzothiophenyl, phthalazinyl, naphthyridinyl, quinoxalyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, where each of these radicals is in particular unsubstituted or mono- or polysubstituted, in particular up to trisubstituted, by substituents selected independently of one another from the substituents mentioned above under "substituted". Preferably, heterocyclyl is an unsaturated ring having 5 or 6 ring atoms, where, in the ring system, one or more heteroatoms, in particular selected from oxygen, nitrogen or sulfur, are present, in particular pyridyl, thienyl or furyl, and where this ring is unsubstituted or mono- or polysubstituted, in particular up to trisubstituted, by lower alkyl, such as ethyl or preferably methyl, lower alkoxy, such as ethoxy or preferably methoxy, or phenyl.

Halogen is in particular fluorine, chlorine, bromine or iodine, in particular chlorine or bromine.

In N-alkylamino or N,N-dialkylamino, alkyl is in particular as defined above. N-Lower alkylamino or N,N-di-lower alkylamino is preferred.

In unsubstituted or substituted arylamino, aryl is preferably as defined above, in particular phenyl or naphthyl, where in the case of substitution, as substituents, one or more, preferably up to three, substituents selected independently of one another from those mentioned above under "substituted" are preferred.

In unsubstituted or substituted alkoxy, alkyl is preferably as defined above, in particular lower alkyl, where in the case of substitution, as substituents, one or more, preferably up to three, substituents selected independently of one another from those mentioned above under "substituted" are preferred.

In unsubstituted or substituted aryloxy, aryl preferably has the abovementioned meanings, in particular phenyl or naphthyl, where in the case of substitution, as substituents, one or more, preferably up to three, substituents selected independently of one another from those mentioned above under "substituted" are preferred.

A 5- or 6-membered ring formed from $R_3$ and $R_4$, together with the carbon atoms connecting them, is in particular a carbocyclic ring, preferably (in the case of compounds of the formulae IA, IB, IIIA, IIIB, IVA and IVB) 1,2-cyclopentylene or 1,2-cyclohexylene or (in the case of compounds of the formula II) 1,2-cyclopent-1,2-enylene or 1,2-cyclohexyl-1,2-enylene (i.e., $R_3$ and $R_4$ form a bridge of the formula —$CH_2$—$CH_2$—$CH_2$— (trimethylene) or of the formula —$CH_2$—$CH_2$—$CH_2$—$CH_2$— (tetramethylene)).

Organic silyl is any possible radical forming an organic silyloxy group with the bonding oxygen, in particular trisubstituted silyl, in which the substituents independently of one another are each an aliphatic, araliphatic, cycloaliphatic or aromatic hydrocarbon radical which is unsubstituted or substituted, e.g. by lower alkyl, lower alkoxy, aryl (in particular phenyl), halogen, and/or nitro, preferably lower alkyl, phenyl-lower alkyl, cycloalkyl or phenyl which is unsubstituted or substituted as described above under "substituted", e.g. tri-lower alkylsilyl, such as trimethylsilyl; triethylsilyl, tert-butyldimethylsilyl, isopropyldimethylsilyl; di-tert-butylmethlsilyl or di-n-butylmethylsilyl, triarylsilyl, such as triphenylsilyl; or phenyl-di-lower alkylsilyl, such as phenyldimethylsilyl:

$R_1$ and $R_6$ are in each case different radicals selected from—in each case unsubstituted or substituted—alkyl, aryl or heterocyclyl, such that the carbon atom bonding these radicals is chiral, where at least one of these radicals is unsubstituted or substituted aryl or unsubstituted or substituted heterocyclyl, preferably aryl.

As a heterogeneous hydrogenation catalyst which can be used for hydrogenation with saturation of the double bond, one or more customary hydrogenation catalysts are preferably used, such as noble metal catalysts on customary support materials (such as argillaceous earth, alumina, titanium dioxide, graphite, silica, carbon (in particular activated carbon), pumice, alkaline earth metal sulfates or alkaline earth metal carbonates), for example Pt on a support material, in particular platinum on zirconium oxide, platinum on argillaceous earth, in particular on alumina, platinum on titanium dioxide, platinum on graphite, platinum on silica, platinum on carbon, platinum on pumice or platinum on an alkaline earth metal sulfate or carbonate, such as barium sulfate or strontium sulfate or calcium carbonate; or else rhodium, ruthenium, palladium or iridium on any desired support materials, in particular those just mentioned for platinum. Furthermore, other suitable heavy metal hydrogenation catalysts can also be used, such as nickel or cobalt, preferably as Raney nickel or Raney cobalt. Platinum on a support material is particularly preferred, in particular on alumina, with which particularly good yields can be achieved, very particularly the catalyst type X 214 XVH/D from the company Degussa AG, Frankfurt/Pullach, Germany; or (somewhat less preferred) the catalyst type 4759 from the company Engelhard Corporation, Iselin, N.J., USA.

The reaction can be carried out at low or elevated temperatures, preferably from −20 to 150° C., in particular from −10 to 100° C., primarily between 10 and 50° C. Lower temperatures in this case bring about improved optical yields, but lower activity, a good compromise existing in particular in the temperature range identified by "primarily". The hydrogenation is in particular carried out at normal pressure or elevated pressure, the pressure can preferably be in the range from $10^5$ to $2 \times 10^7$ Pa (Pascal), in particular between $5 \times 10^5$ and $10^7$ Pa. Primarily, the hydrogenation is carried out at elevated pressure, higher pressures afford higher conversions and slightly improved selectivity. The catalytic amount of catalyst is preferably 0.0001 to 10% by weight, in particular 0.001 to 10% by weight, especially 0.01 to 5% by weight based on the compound of the formula II to be hydrogenated. The particularly preferred catalyst with Pt on alumina is already wholly adequately active in amounts of below 0.1%, in particular between 0.01 and 0.06%. This makes possible marked cost reduction because of reduction in the amount of the noble metal needed.

The hydrogenation takes place in the absence or, preferably, presence of an inert solvent, in particular of an inert organic solvent, it being possible to employ individual solvents or solvent mixtures. Suitable solvents are, for example, aliphatic hydrocarbons, such as pentane, hexane or petroleum ether, cycloaliphatic hydrocarbons, such as cyclohexane or methylcyclohexane, or aromatic hydrocarbons, such as benzene, toluene or xylene, aliphatic halohydrocarbons, such as methylene chloride, chloroform, di- or tetrachloroethane, nitriles, such as acetonitrile, propionitrile or benzonitrile, ethers, such as diethyl ether, dibutyl ether, tert-butyl methyl ether, ethylene glycol dimethyl ether, ethylene glycol diethyl ether, diethylene glycol monoethyl ether, tetrahydrofuran, dioxane, diethylene glycol monomethyl ether or monoethyl ether, ketones, such as acetone or methyl isobutyl ketone, carboxylic acid esters or lactones, such as ethyl acetate or methyl acetate or valerolactone, N-substituted lactams, such as N-methylpyrrolidone, carboxamides, such as dimethylacetamide or dimethylformamide, acyclic ureas, such as dimethylimidazoline, sulfoxides or sulfones, such as dimethyl sulfoxide, dimethyl sulfone, tetramethylene sulfoxide or tetramethylene sulfone, or in particular alcohols, such as hydroxy-lower alkanes, preferably methanol, ethanol, propanol, butanol, or ethylene glycol lower alkyl ethers, such as ethylene glycol monomethyl ether, ethylene glycol monoethyl ether or diethylene glycol monomethyl ether; or water, or mixtures of two or more such solvents.

The hydrogenation is preferably carried out such that the catalyst is introduced and then the substrate, if desired also reaction auxiliaries, is added and hydrogen is injected and then the reaction is allowed to proceed. The process can be carried out in any suitable types of reactor, for example continuously or batchwise.

The hydrogenation, in particular under the most strongly preferred conditions, preferably yields a diastereomeric excess of one of the two compounds of the formula IIA or IIB of more than 50%, in particular of more than 55%.

An acid radical X in an acid of the formula $[H^+]_n X^{n-}$ is in particular an inorganic acid radical, preferably a halide radical (n=1), in particular $Cl^-$, $Br^-$ or $I^-$, or furthermore a perchlorate radical ($ClO_4^-$) (n=1), nitrate radical ($NO_3^-$) (n=1) hydrogensulfate radical ($HSO_4^-$) (n=1), a sulfate radical ($SO_4^{2-}$) (n=2), or a dihydrogenphosphate radical ($H_2PO_4^-$) (n=1), a hydrogencarbonate radical ($HCO_3^-$) (n=1) or a monohydrogenphosphate radical ($HPO_4^-$) (n=2), or an organic acid radical, in particular of a carboxylic acid, such as trifluoroacetic acid, acetic acid or formic acid (in each case n=1), or of a sulfonic acid, in particular of an arylsulfonic acid, such as benzenesulfonic acid, o- or p-toluenesulfonic acid, of a mono-, bi- or tricycloalkylsulfonic acid, such as camphorsulfonic acid, or of an alkanesulfonic acid, such as methanesulfonic acid, ethanesulfonic acid or trifluoromethanesulfonic acid (in each case n=1).

X=halogen and thus n=1 is preferred.

The conversion of a compound of the formula IIA and/or IIB into a (diastereomeric) acid addition salt of the formula IIIA or IIIB is preferably carried out in a polar solvent, in particular an ether, such as dioxane or tetrahydrofuran, or primarily an alcohol, such as methanol, ethanol or in particular isopropanol, in the presence of the acid of the formula $[H^+]_n X^{n-}$. In a preferred variant of this step, the base is introduced in the (preferably warmed) solvent and treated with the acid in the same solvent. The temperatures for the reaction are preferably in the range from 0° C. up to the boiling temperature of the reaction mixture concerned, in particular at the boiling point.

By cooling, the crystallization of the products of the formula IIIA or IIIB is initiated and carried out, which leads to the separation of the diastereomers from the diastereomer mixtures. By means of seeding, the crystallization can be facilitated and, when using seed crystals having high diastereomeric purity, also the diastereomeric purity of the product of the formula IIIA or IIIB, so that the procedure of seeding with the desired product is particularly preferred. Preferably, the product obtained is then additionally recrystallized further times from the same or a similar solvent, in particular once to at most twice. The recrystallization is preferably carried out in an aliphatic alcohol having up to 7, preferably up to 4 carbon atoms, such as methanol, ethanol or (in particular iso)propanol, it being possible (in particular in the case of methanol) to initiate the crystallization process by addition of ketones, such as acetone, or carboxylic acid esters, such as ethyl acetate. Mixtures of chlorinated hydrocarbons, such as chloroform or methylene chloride, with ketones or carboxylic acid esters are also suitable.

The salt formation and recrystallization, in particular under the conditions identified as preferred, preferably produces a yield of 60% or more and a diastereomeric excess of more than 98%.

The removal of the chiral auxiliary group $R_1R_6CH$— is carried out according to customary methods, primarily by hydrogenolysis. As a catalyst, one of those mentioned above for the hydrogenation of compounds of the formula II can be employed; the hydrogenolysis is preferably carried out in the presence of palladium on one of the abovementioned support materials, in particular using palladium on carbon (Pd/C), preferably using 2 to 15% Pd on carbon, especially 5 to 10% Pd on carbon. The amount of catalyst can be markedly lower than in previously known processes and is preferably 0.001 to 5%, in particular 0.05 to 0.2%, in each case based on the amount of substrate of the formula IIIA or IIIB. As solvents, polar solvents or solvent mixtures are preferably used, in particular water and/or alcohols, such as propanol, ethanol or in particular methanol. The hydrogen can be under normal pressure or elevated pressure; the reaction is preferably carried out at pressures between $10^5$ and $2\times10^6$ Pa. Lower pressures are advantageous; pressures between $10^5$ and $2\times10^5$ Pa are particularly preferred. The temperature is preferably in the slightly elevated range, in particular between 50 and 80° C., preferably between 55 and 75° C. Other customary processes for the removal of the chiral auxiliary group can also be used, thus, for example, 1-(p-lower alkoxyphenyl)ethyl can also be removed by acid catalysis.

The optional conversion of the acid addition salts of the formula IVA or IVB into the free bases takes place, if desired, subsequently in the presence of a base and leads to the free compounds of the formula IA or IB. The conversion takes place under customary conditions. As a base, it is possible to use, for example, ammonia or a metal, in particular alkali metal hydroxide, carbonate or hydrogencarbonate. The neutralization can also be carried out on a basic anion exchanger. Suitable solvents are polar solvents, such as water or alcohols, such as methanol or ethanol, or mixtures of solvents of this type. Since the salts can be stored particularly well, the conversion into the free compounds of the formula IA or IB is often not carried out.

The optional removal of the radical $R_5$ takes place, if desired, under conditions known per se, for example by hydrolysis, preferably in acidic medium at elevated temperatures, in particular in the range from 50 to 100° C., for example at 80 to 90° C. As an acidic medium, mineral acids, such as hydrochloric acid, preferably concentrated hydrochloric acid, are preferred. After customary work up, the products of the formula IA or IB are obtained in the form of their acid addition salts, which can further be converted into the free form by neutralization of the hydrochloride, for example with ammonia or an organic amine (which can also be present as an internal salt).

If $R_5$ is equal to H, the products of the formula IA or IB can also be present as internal salts.

The reaction to give the salts of the formula IVA or IVB without subsequent conversion into the free compounds of the formula IA or IB and without removal of $R_5$, if $R_5$ has another of the meanings mentioned apart from hydrogen, is preferred.

By means of the chosen sequences (firstly removal of the chiral auxiliary group, then neutralization to give the free compounds of the formula IA or IB), the yield of the two reactions can be increased to more than 90%, in particular to more than 99%. The resulting enantiomeric excess in the case of the compounds of the formula IA or IB is preferably more than 98%, in particular more than 99%.

The starting compounds of the formula (II) are known or can be obtained in analogy to known processes, for example the processes disclosed in EP-0144980.

PREFERRED EMBODIMENTS OF THE INVENTION

In the following preferred embodiments of the invention, more general substituent meanings or definitions (for example for reaction conditions) can in each case be replaced individually, severally or totally by the substituent meanings or definitions identified above as preferred, which in each case leads to preferred embodiments.

Preferably, the invention relates to (i) a process starting from compounds of the formula II via those of the formulae IIA and IIB to those of the formulae IIIA and/or IIIB, then via those of the formulae IVA and/or IVB and, if desired, the subsequent conversion into the free compounds of the formula IA or IB, such as described above or below; or (ii) a process for the removal of the chiral auxiliary group from an acid addition salt of the formula IIIA or IIIB to give a salt of the formula IVA or IV and, if desired, the subsequent conversion into the free compounds of the formula IA or IB in the presence of a base, such as described above or below; or (iii) a process for the preparation of compounds of the formulae IIA and/or IIB by hydrogenation of a compound of the formula II in the presence of platinum on alumina as a catalyst;

the substituents in the compounds of the formulae IA, IB, II, IIA, IIB, IIIA, IIIB, IVA and IVB, and X and n, in each case if present, having the following meanings:

$R_2$, $R_3$ and $R_5$ independently of one another are $C_1$–$C_{10}$alkyl, which is unsubstituted or, if substituted, substituted by phenyl, which is unsubstituted (preferred) or further substituted by $C_1$–$C_4$alkyl, $C_1$–$C_4$alkoxy, $C_1$–$C_4$alkylamino, halogen or hydroxyl, in particular by $C_1$–$C_4$alkyl, such as ethyl or in particular methyl, or $C_1$–$C_4$alkoxy, such as ethoxy or in particular methoxy; a preferred $C_1$–$C_{10}$alkyl radical being $C_1$–$C_4$alkyl substituted as above or in particular unsubstituted—a suitable $C_1$–$C_{10}$alkyl radical substituted by phenyl in particular being benzyl;

or $R_3$ is alternatively phenyl, which is unsubstituted (preferred) or further substituted by $C_1$–$C_4$alkyl, $C_1$–$C_4$alkoxy, $C_1$–$C_4$alkylamino, halogen or hydroxyl, in particular by $C_1$–$C_4$alkyl, such as ethyl or in particular methyl, or $C_1$–$C_4$alkoxy, such as ethoxy or in particular methoxy, in particular phenyl or 4-methoxyphenyl;

or $R_3$ is unsaturated heterocyclyl, which has 5 or 6 ring atoms, of which one or more, preferably up to two, are selected from the group consisting of O, N and S, the heterocyclyl radicals being unsubstituted or substituted, for example, by $C_1$–$C_4$alkyl, halogen or phenyl or (preferably) unsubstituted; in particular pyridyl, thienyl and furyl;

or $R_3$ is $C_1$–$C_{10}$alkyl substituted by one or more fluorine atoms, in particular perfluoro-lower alkyl, such as trifluoromethyl;

$R_4$ is hydrogen; or $C_1$–$C_{10}$alkyl, in particular lower alkyl; preferably hydrogen;

$R_1$ and $R_6$ are two radicals which are different from one another selected from $C_1$–$C_{10}$alkyl, which is unsubstituted or substituted by phenyl, which for its part is unsubstituted (preferred) or further substituted by $C_1$–$C_4$alkyl, $C_1$–$C_4$alkoxy, $C_1$–$C_4$alkylamino, halogen or hydroxyl, in particular by $C_1$–$C_4$alkyl, such as ethyl or in particular methyl, or $C_1$–$C_4$alkoxy, such as ethoxy or in particular methoxy; a preferred $C_1$–$C_{10}$alkyl radical being $C_1$–$C_4$alkyl—a suitable $C_1$–$C_{10}$alkyl radical substituted by phenyl in particular being benzyl; and from phenyl, which is unsubstituted (preferred) or further substituted by $C_1$–$C_4$alkyl, $C_1$–$C_4$alkoxy, $C_1$–$C_4$alkylamino, halogen or hydroxyl, in particular by $C_1$–$C_4$alkyl, such as ethyl or in particular methyl, or $C_1$–$C_4$alkoxy, such as ethoxy or in particular methoxy; with the proviso that at least one of the radicals $R_1$ and $R_6$ is phenyl, which is substituted as just described or is preferably unsubstituted;

n is equal to 1 and

X is a (monobasic) acid radical, preferably halogen, in particular chlorine.

More strongly preferred is a process (i), (ii) or (iii), as defined in the above section, the substituents in the compounds of the formula IA, IB, II, IIA, IIB, IIIA, IIIB, IVA and IVB, and X and n, in each case if present, having the following meanings:

$R_2$ is hydrogen or $C_1$–$C_{10}$alkyl unsubstituted or substituted by phenyl, in particular hydrogen or $C_1$–$C_4$alkyl unsubstituted or substituted by phenyl, in particular hydrogen, benzyl or $C_1$–$C_4$alkyl, especially hydrogen;

$R_3$ is phenyl or $C_1$–$C_4$alkyl unsubstituted or substituted by phenyl or one or more fluorine atoms, the two phenyl radicals mentioned in each case being unsubstituted or substituted by $C_1$–$C_4$alkyl, $C_1$–$C_4$alkoxy, $C_1$–$C_4$alkylamino, halogen or hydroxyl; preferably phenyl unsubstituted or substituted by $C_1$–$C_4$alkyl, $C_1$–$C_4$alkoxy, $C_1$–$C_4$alkylamino, halogen or hydroxyl or $C_1$–$C_{10}$alkyl unsubstituted or substituted by phenyl, in particular $C_1$–$C_4$alkyl unsubstituted or substituted by phenyl; primarily substituted or unsubstituted phenyl as indicated above, or in particular $C_1$–$C_4$alkyl or benzyl, especially $C_1$–$C_4$alkyl, in particular methyl, ethyl, n-propyl, isopropyl, n-butyl, isobutyl, sec-butyl or tert-butyl;

$R_4$ is hydrogen or $C_1$–$C_{10}$alkyl, in particular hydrogen or $C_1$–$C_4$alkyl, preferably hydrogen;

$R_5$ is hydrogen or $C_1$–$C_{10}$alkyl, in particular $C_1$–$C_{10}$alkyl, preferably $C_1$–$C_4$alkyl; primarily $R_5$ is tert-butyl, methyl or ethyl, especially ethyl or primarily methyl;

and $R_1$ and $R_6$ are in each case phenyl or $C_1$–$C_{10}$alkyl unsubstituted or substituted by phenyl, the two phenyl radicals mentioned in each case being unsubstituted or substituted by $C_1$–$C_4$alkyl, $C_1$–$C_4$alkoxy, $C_1$–$C_4$alkylamino, halogen or hydroxyl; with the proviso that $R_1$ and $R_6$ are different from one another and one of the radicals is phenyl or phenyl substituted as just described; preferably $R_1$ is equal to phenyl or $C_1$–$C_4$alkoxy (in particular methoxy)phenyl and $R_6$ is $C_1$–$C_4$alkyl, in particular methyl; very preferably $R_1$ and $R_2$, together with the bonding CH, form (R)- or (S)-1-phenylethyl;

n is equal to 1 and

X is an inorganic acid radical, preferably halogen, in particular chlorine.

More strongly preferred is a process (i), (ii) or (iii), such as defined in the penultimate section, the substituents in the compounds of the formulae IA, IB, II, IIA, IIB, IIIA, IIIB, IVA and IVB, and X and n, in each case if present, having the following meanings:

$R_2$ is hydrogen or $C_1$–$C_{10}$alkyl unsubstituted or substituted by phenyl;

$R_3$ is phenyl or $C_1$–$C_{10}$alkyl substituted by phenyl or preferably unsubstituted, the respective phenyl radicals being unsubstituted or substituted by $C_1$–$C_4$alkyl, $C_1$–$C_4$alkoxy, $C_1$–$C_4$alkylamino, halogen or hydroxyl;

$R_4$ and $R_5$ are in each case hydrogen or $C_1$–$C_{10}$alkyl;

$R_1$ is $C_1$–$C_{10}$alkyl;

$R_6$ is phenyl;

n is 1 and

X is halogen, in particular chlorine.

Very particularly preferred is a process (i), (ii) or (iii), as defined in the pre-penultimate section, the substituents in the compounds of the formulae IA, IB, II, IIA, IIB, IIIA, IIIB, IVA and IVB, and X and n, in each case if present, having the following meanings:

$R_2$ and $R_4$ are hydrogen;

$R_3$ is phenyl unsubstituted or substituted by $C_1$–$C_4$alkyl, $C_1$–$C_4$alkoxy, $C_1$–$C_4$alkylamino, halogen or hydroxyl or $C_1$–$C_{10}$alkyl substituted by phenyl or preferably unsubstituted, in particular methyl, ethyl, n-propyl, isopropyl, n-butyl, isobutyl, sec-butyl or tert-butyl;

$R_5$ is $C_1$–$C_4$alkyl;

$R_1$ is $C_1$–$C_4$alkyl;

$R_6$ is phenyl;

n is 1 and

X is halogen, in particular chlorine.

Very particularly preferred is a process (i), (ii) or (iii), such as defined in the fourth-last section, the substituents in the compounds of the formulae IA, IB, II, IIA, IIB, IIIA, IIIB, IVA and IVB, and X and n, in each case if present, having the following meanings:

$R_2$ and $R_4$ are hydrogen, $R_3$ is phenyl unsubstituted or substituted by $C_1$–$C_4$alkyl, $C_1$–$C_4$alkoxy, $C_1$–$C_4$alkylamino, halogen or hydroxyl or $C_1$–$C_4$alkyl substituted by phenyl or preferably unsubstituted, in particular methyl, ethyl, n-propyl, isopropyl, n-butyl, isobutyl, sec-butyl or tert-butyl;

$R_5$ is $C_1$–$C_4$alkyl, in particular methyl, ethyl or tert-butyl;

$R_1$ is $C_1$–$C_4$alkyl;

$R_6$ is phenyl;

n is 1 and

X is halogen, in particular chlorine.

Preferred processes are those mentioned above under "preferred embodiments" in which for the individual process steps the process conditions (amounts of reactants, temperatures, catalysts, solvents, pressures and the like) which are characterized under the definitions by "preferred", "preferably", "in particular", "primarily", "especially" or the like as preferred, in particular the most strongly preferred variants in each case, are used.

A very preferred process is one according to a paragraph mentioned above under "preferred embodiments" for the preparation of compounds of the formula IA or IB, selected from the compounds having the formulae IA* and IB*,

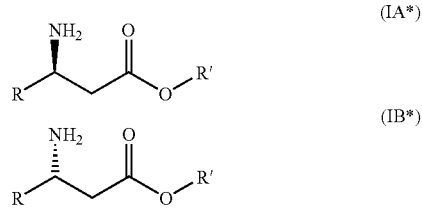

in which R is methyl, isopropyl, phenyl, p-methoxyphenyl, sec-butyl, trifluoromethyl or benzyl; and R' is hydrogen, methyl, ethyl or isopropyl;
or acid addition salts thereof,
wherein the appropriately substituted starting compounds are used, the radical of the formula R₆R₁CH—, if this is present in the corresponding starting and intermediate compounds, used being one of the formula

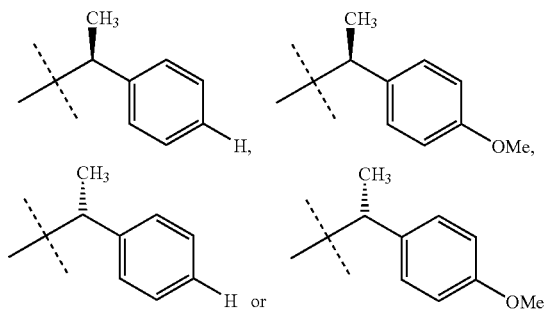

Very preferred compounds, process steps and sequences of process steps are those mentioned in the examples.

The following examples serve to illustrate the invention without restricting its scope.

EXAMPLE 1

Hydrogenation of the Double Bond in Compounds of the Formula II

The amount of starting material x* in each case indicated in the Table is added to the catalyst (5% Pt/Al₂O₃ catalyst F 214 XVH/D, Degussa AG, Frankfurt/Pullach, Germany), which (based on the amount by weight of the starting material) is employed in the indicated relative amount (=substrate/catalyst), in methanol as a solvent. With stirring, hydrogen is injected at the pressure indicated and the mixture is stirred at the temperature indicated for the time indicated. After blowing out with argon, the reaction mixture is filtered and evaporated to dryness.

The analysis of the product yield and of the diastereomeric excess {DE=100×([diastereomer 1]–[diastereomer 2])/([diastereomer 1]+[diastereomer 2]), [diastereomer. (i)] being the molar amount of the diastereomer concerned and [diastereomer1]>[diastereomer 2]} being carried out by ¹H-NMR (in CDCl₃, 300 MHz).

Formulae of the Compounds:

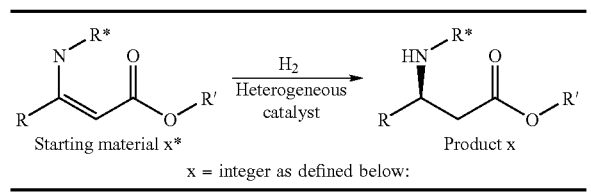

| R = | x = |
|---|---|
| Ethyl | 1 |
| Methyl | 2 |
| Isopropyl | 3 |
| Ph | 4 |
| p-OMe—Ph | 5 |
| sec-Butyl | 6 |

-continued

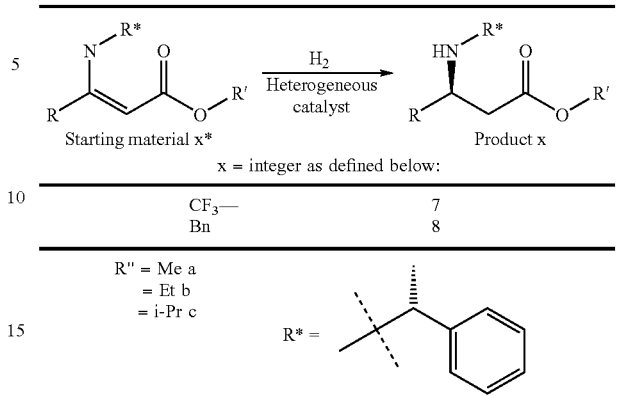

| | x |
|---|---|
| CF₃— | 7 |
| Bn | 8 |

R'' = Me a
= Et b
= i-Pr c

The following results are obtained

TABLE 1

| Starting material (amount) | Product | Substrate/ catalyst (weight ratio) | Conc. of substrate (% by weight) | Pressure (bar) | Temperature (° C.) | Product purity NMR | Diastereomeric excess NMR |
|---|---|---|---|---|---|---|---|
| 2b* | 2b | 5/1 | 9 | 100 | 25 | >99% | 73% |
| 2a* | 2a | 5/1 | 9 | 20 | 25 | >99% | 60% |
| 3b* | 3b | 5/1 | 9 | 100 | 25 | >90% | 55% |
| 3a* | 3a | 5/1 | 9 | 100 | 25 | >93% | 54% |
| 4b* | 4b | 5/2 | 9 | 100 | 20 | 50% | 59% |
| 5b* | 5b | 5/2 | 9 | 100 | 20 | 74% | 71% |
| 6b* | 6b | 5/1 | 23 | 100 | 25 | 80% | 69% |
| 7c* | 7c | 1/1 | 5 | 100 | 45 | 55% | 71% |
| 8a* | 8a | 5/1 | 23 | 100 | 25 | >99% | 70% |
| 2a* (375 μl) | 2a | 63/1 | 33 | 20 | 35 | >99% | 59% |
| 2a* (7 g) | 2a | 50/1 | 33 | 20 | 35 | >99% | 53% |
| 3a* (375 μl) | 3a | 15/1 | 33 | 20 | 35 | >98% | 68% |
| 3a* (7g) | 3a | 25/1 | 33 | 20 | 35 | >98% | 68% |

EXAMPLE 2

Example of Preparative Hydrogenation of the C═C Bond in a Compound of the Formula II 140 mg of 5% Pt/Al₂O₃ F 214 XVH/D catalyst are placed in a 50 ml autoclave (current breaker, magnetic stirring fish). After addition of 7 g of substrate 1a* dissolved in 14 ml of methanol (see Example 1), the autoclave is closed and injected with argon, then 20 bar (20×10⁵ Pa) of hydrogen are injected and the mixture is warmed to 35° C. After hydrogenation for 18 hours at 35° C., the reaction is terminated. The catalyst is filtered off and the methanol is evaporated under reduced pressure. The product 1a obtained is analysed. A yield of 97% with a diastereomeric excess of 66% is determined by NMR.

EXAMPLE 3

Synthesis of the HCl Salt and Crystallization of a Compound of the Formula IIIA 100 g of 1a (see Examples 1 and 2) are dissolved in 1 l of isopropanol. After heating to reflux temperature, 170 ml of a 2.5 molar solution of hydrogen chloride in isopropanol are added. The reaction mixture turns yellow. The boiling solution is then slowly cooled and seeded with diastereomerically pure HCl salt of the compound 1a until the product begins to crystallize at 65 to 70° C. In the course of 2 hours, the mixture is cooled to room temperature and the resulting crystals are filtered off, washed twice with small amounts of isopropanol and dried in vacuo. Yield: 81.6 g (71%) with a 96% diastereomeric excess. The product P1a is again recrystallized from 1.6 l of isopropanol, and the product suspension is cooled to 0° C., filtered and the crystals are dried in vacuo (yield 74.2%=64% in total) with a diastereomeric excess of more than 98% (NMR).

Formula P1a:

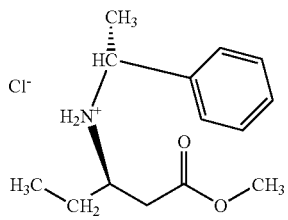

EXAMPLE 4

Preparation of an Acid Addition Salt of the Formula IVA by Removal of the Chiral Auxiliary Group 30 mg of 10% Pd/C E 4505 (Engelhard Corporation, Iselin, N.J., USA) are introduced into a 50 ml autoclave (current breaker, magnetic stirring fish). After addition of a solution of 4.5 g of substrate P1a (Example 4) in a mixture of 13.5 ml of methanol and 1.5 ml of water, the autoclave is closed and injected with argon. Hydrogen is then injected at a pressure of 1 to 2 bar ($1-2\times10^5$ Pa) and the mixture is heated with stirring to 55° C. After hydrogenation for 18 hours at 55° C., the reaction is terminated, the catalyst is filtered off and the methanol/water is evaporated under reduced pressure. The final product FP1a is obtained in a yield of 4.5 g (>98%) and with an enantiomeric excess (ee) of 99%.

Formula FP1a:

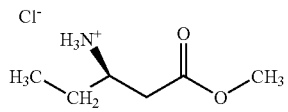

The invention claimed is:

1. A process for the preparation of optically active compounds of the formula IA or IB

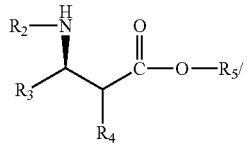

(IA)

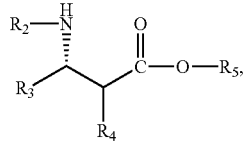

(IB)

as free bases or as acid addition salts thereof, in which
$R_2$ is hydrogen,
$R_3$ is—in each case unsubstituted or substituted—phenyl or $C_1-C_4$alkyl,
$R_4$ is hydrogen or $C_1-C_{10}$alkyl, and
$R_5$ is hydrogen or $C_1-C_4$alkyl,
which process comprises
(a) hydrogenating a compound of the formula II

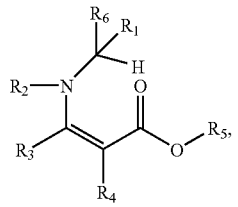

(II)

in which
$R_1$ is hydrogen or $C_1-C_4$alkyl, and $R_6$ is unsubstituted or substituted phenyl, and
$R_2$, $R_3$, $R_4$ and $R_5$ are as defined for compounds of the formula IA or IB, in the presence of a catalytically active amount of a heterogeneous platinum on alumina hydrogenation catalyst with saturation of the double bond to give compounds of the formulae IIA and/or IIB,

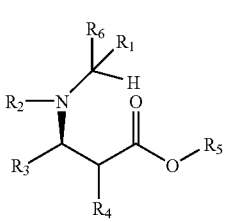

(IIA)

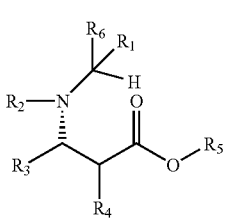

(IIB)

in which the radicals $R_1$ and $R_6$ are as defined for compounds of the formula II and the radicals $R_2$, $R_3$, $R_4$ and $R_5$ are as defined for compounds of the formulae IA and IB;

(b) then converting the product obtained with an acid of the formula $[H^+]_n X^{n-}$, in which n is 1 and X is an acid radical, into a corresponding acid addition salt of the formula(e) IIIA and/or IIIB,

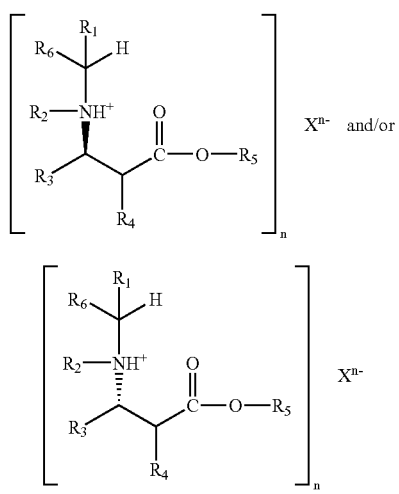

in which n is 1, $X^{n-}$ is an acid anion, $R_1$ and $R_6$ are as defined for compounds of the formula II, and $R_2$, $R_3$, $R_4$ and $R_5$ are as defined for compounds of the formulae IA and IB; which is (c) converted by removal of the chiral auxiliary group $R_1R_6CH$— into a corresponding salt of the formula(e) IVA and/or IVB

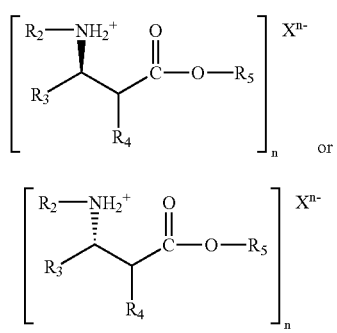

in which n and the radicals $R_2$ to $R_5$ and $X^{n-}$ are as defined above, and, optionally, (d) the acid addition salt of the formula IVA or IVB obtained is converted in the presence of a base into the free compounds of the formula IA or IB; and/or, optionally, the group $R_5$ is removed from an ester of the formula IVA or IVB, if $R_5$ is not hydrogen.

2. A process according to claim 1 for the preparation of optically active compounds of the formula IA or IB shown in claim 1 as free bases or as acid addition salts thereof, in which the acid addition salt of the formula IIIA or IIIB shown in claim 1 obtained is crystallized;

then the chiral auxiliary group $R_1R_6CH$— is removed, and thus a corresponding salt of the formula IVA or IVB shown in claim 1 is obtained.

3. A process according to claim 1 for the preparation of compounds of the formula IA or IB, the substituents in the compounds of the formulae IA, IB, II, IIA, IIB, IIIA, IIIB, IVA and IVB, and X and n, in each case if present, being as defined below:

$R_2$ and $R_4$ are hydrogen;

$R_3$ is phenyl unsubstituted or substituted by $C_1$–$C_4$alkyl, $C_1$–$C_4$alkoxy, $C_1$–$C_4$alkylamino, halogen or hydroxyl; or is $C_1$–$C_4$alkyl unsubstituted or substituted by phenyl;

$R_5$ is $C_1$–$C_4$alkyl;

$R_1$ is $C_1$–$C_4$alkyl;

$R_6$ is phenyl;

n is 1 and

X is halogen.

4. A process according to any one of claims 1, 2 or 3 for the preparation of compounds of the formula IA or IB, selected from the compounds having the formulae IA* and IB*,

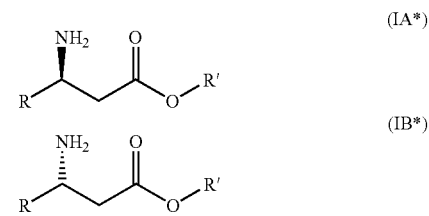

in which R is methyl, isopropyl, phenyl, p-methoxyphenyl, sec-butyl, trifluoromethyl or benzyl; and R' is hydrogen, methyl, ethyl or isopropyl;

or acid addition salts thereof, wherein the appropriately substituted starting compounds are used, the radical of the formula $R_6R_1CH$—, if this is present in the corresponding starting and intermediate compounds, used being one of the formula

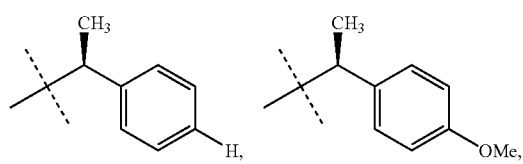

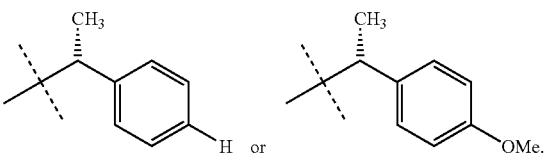

5. A process according to claim 1 wherein the removal of the chiral auxiliary group from compounds of the formula IIIA or IIIB takes place by hydrogenolysis in the presence of palladium on a support material.

6. A process for the preparation of a compound of the formula IIA and/or IIB shown in claim 1, in which the radicals are as defined in the claim, by catalytic hydrogenation of a compound of the formula II shown in claim 1, wherein the catalyst used is platinum on alumina.

7. A process according to claim 1 whereby a pharmaceutically active compound is obtained.

* * * * *